US00PP16646P2

(12) United States Plant Patent
Trees

(10) Patent No.: US PP16,646 P2
(45) Date of Patent: Jun. 13, 2006

(54) ***NEMESIA* PLANT NAMED 'BALARIMDEP'**

(50) Latin Name: *Nemesia caerula*
Varietal Denomination: Balarimdep

(75) Inventor: Scott C. Trees, Shell Beach, CA (US)

(73) Assignee: Ball Horticultural Company, West Chicago, IL (US)

( * ) Notice: Subject to any disclaimer, the term of this patent is extended or adjusted under 35 U.S.C. 154(b) by 87 days.

(21) Appl. No.: 11/022,958

(22) Filed: Dec. 27, 2004

(51) Int. Cl.
*A01H 5/00* (2006.01)

(52) U.S. Cl. ..... Plt./263
(58) Field of Classification Search ..... Plt./263
See application file for complete search history.

*Primary Examiner*—Anne Marie Grunberg
(74) *Attorney, Agent, or Firm*—Wood, Phillips, Katz, Clark & Mortimer

(57) ABSTRACT

A new and distinct cultivar of *Nemesia* plant named 'Balarimdep' characterized by its dark lavender blue-colored flowers, medium green-colored foliage, and heavily branched and upright growth habit.

1 Drawing Sheet

Latin name of genus and species of plant claimed: *Nemesia caerula.*
Variety denomination: 'Balarimdep'.

BACKGROUND OF THE INVENTION

The present invention relates to a new and distinct cultivar of *Nemesia* plant botanically known as *Nemesia caerula* and hereinafter referred to by the cultivar name 'Balarimdep'.

The new cultivar originated in a controlled breeding program in Arroyo Grande, Calif. during August 2000. The objective of the breeding program was the development of *Nemesia* cultivars with a well-branched, spreading growth habit, unique flower colors, and continuous flowering.

The new cultivar was the result of the open-pollination of the *Nemesia caerula* variety Valley Heart Purple, not patented, characterized by its medium lavender-blue-colored flowers and loosely branched habit. The new cultivar was discovered and selected by the inventor as a single flowering plant within the progeny of the above stated open-pollination during January 2001 at Arroyo Grande, Calif.

Asexual reproduction of the new cultivar by terminal stem cuttings since January 2001 at Arroyo Grande, Calif. and West Chicago, Ill. has demonstrated that the new cultivar reproduces true to type with all the characteristics, as herein described, firmly fixed and retained through successive generations of such asexual propagation.

SUMMARY OF THE INVENTION

The following characteristics of the new cultivar have been repeatedly observed and can be used to distinguish 'Balarimdep' as a new and distinct cultivar of *Nemesia* plant:

1. Dark lavender blue-colored flowers with yellow "eye".
2. Medium green-colored foliage.
3. Heavily branched and upright growth habit.

Plants of the new cultivar differ from plants of the female parent primarily in flower color and branching habit.

Of the *Nemesia* cultivars known to the inventor, the most similar to the new cultivar is 'Balardeblu', not patented. However, in side by side comparisons, plants of the new cultivar differ from plants of 'Balardeblu' in the following characteristics:

1. The flowers of the new cultivar are a lighter violet color than the flowers of 'Balardeblu'.
2. Plants of the new cultivar have smaller foliage than plants of 'Balardeblu'.

The new cultivar can also be compared to the cultivar Safari Plum, not patented. However, in side by side comparisons, plants of the new cultivar differ from plants of 'Safari Plum' in the following characteristics:

1. Plants of the new cultivar are taller than plants of 'Safari Plum'.
2. Plants of the new cultivar have smaller leaves than plants of 'Safari Plum'.
3. Plants of the new cultivar have smaller flowers than plants of 'Safari Plum'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which more accurately describe the colors of 'Balarimdep'. The plants were grown in 10 cm pots for 9 weeks in a greenhouse at West Chicago, Ill.

DETAILED BOTANICAL DESCRIPTION

Figure 1:
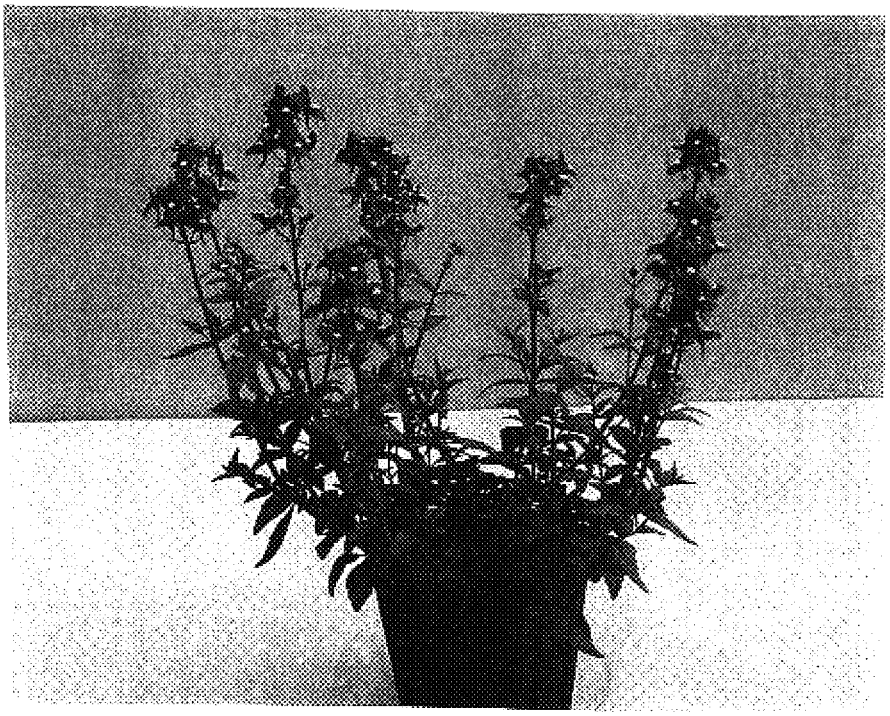
FIG. 1 illustrates the overall growth and flowering habit of 'Balarimdep'.
Figure 2:
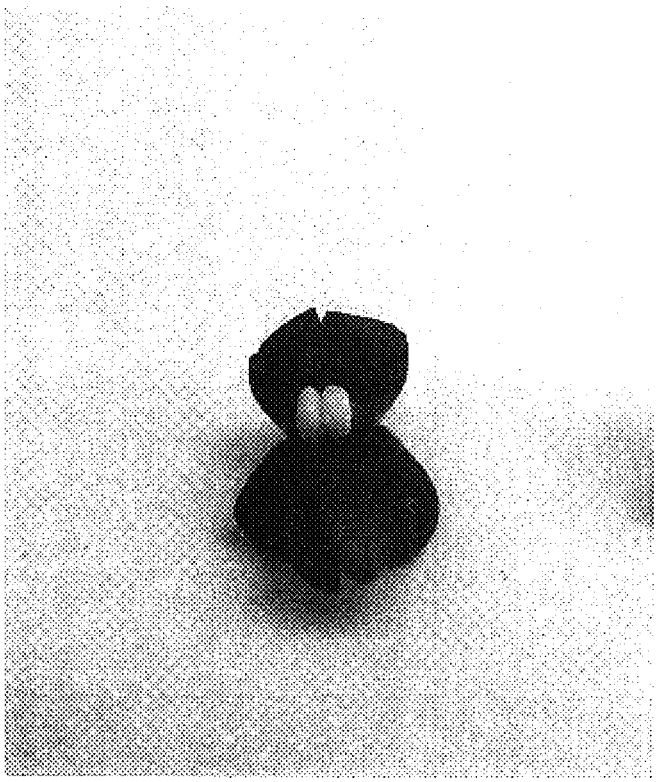
FIG. 2 illustrates a close-up view of an individual flower of 'Balarimdep'.

The new cultivar has not been observed under all possible environmental conditions to date. Accordingly, it is possible that the phenotype may vary somewhat with variations in the environment, such as temperature, light intensity, and day length without, however, any variance in genotype.

The chart used in the identification of colors described herein is The R.H.S. Colour Chart of The Royal Horticultural Society, London, England, 2001 edition, except where general color terms of ordinary significance are used. The color values were determined on Sep. 24, 2004 between 1:00 and 3:00 p.m. under natural light conditions.

The following descriptions and measurements describe plants produced from cuttings taken from stock plants and grown in a double polycarbonate-covered greenhouse under conditions comparable to those used in commercial practice. The plants were grown in 10 cm pots for 9 weeks while utilizing a soil-less growth medium. Greenhouse temperatures were maintained at approximately 65° to 75° F. (18° to 24° C.) during the day and approximately 50° to 60° F. (10° to 15° C.) during the night. Daytime greenhouse light levels were maintained at approximately 4,000 to 7,000 foot-candles.

Botanical classification: *Nemesia caerula,* cultivar Balarimdep.

Parentage: Open-pollination of the *Nemesia* variety Valley Heart Purple, not patented.

Propagation:

*Type cutting.*—Terminal stem.

*Time to initiate roots.*—Approximately 6 to 9 days.

*Time to produce a rooted cutting.*—Approximately 21 to 28 days.

*Root description.*—Fine and fibrous.

*Rooting habit.*—Branching.

Plant description:

*Crop time.*—Approximately 5–7 weeks from a rooted cutting.

*Habit of growth.*—Moderately vigorous with good branching.

*Form.*—Upright and outwardly spreading.

*Size.*—Height from soil level to top of foliage: Approximately 23.9 cm. Diameter (area of spread): Approximately 37.6 cm.

*Branch.*—Quantity: Approximately 8 primary branches with laterals at every node. Strength of all branches: Moderate. Shape of all branches: Square in cross section. Appearance of all branches: Wiry. Length of primary branch: Approximately 27.4 cm. Diameter of primary branch: Approximately 2 mm. Texture of all branches: Glabrous. Color of all branches: 144A. Internode length at middle of primary branch: Approximately 2.6 cm.

*Foliage.*—Quantity per branch: Approximately 12. Fragrance: None. Type: Simple. Arrangement: Opposite. Orientation to stem: Right angle. Shape: Ovate. Apex: Acute. Base: Obtuse. Margin: Serrate. Venation pattern: Palmate. Length of leaf taken from middle of branch: Approximately 2.7 cm. Leaf width: Approximately 1.1 cm. Texture of upper and lower surfaces: Glabrous. Color of mature foliage: Upper surface: 137A with venation of 144A. Lower surface: 147B with venation of 144A. Petiole length: Approximately 2 mm. Petiole diameter: Approximately 1.8 mm. Petiole texture: Glabrous. Petiole color: 144A.

Flowering description:

*Time to first flower.*—Approximately 7 weeks from a rooted cutting.

*Flowering habit.*—Freely flowering under outdoor growing conditions with substantially continuous blooming from spring through autumnl and year round in greenhouse environment.

Inflorescence description:

*Type.*—Terminal clutsters.

*Size.*—Depth: Approximately 4.9 cm. Diameter: Approximately 3.3 cm.

*Number per plant.*—Approximately 16 fully open racemes and 8 developing racemes.

*Number of fully open flowers per raceme at any one time.*—Approximately 9.

Flower description:

*Type.*—Solitary, zygomorphic, and bilabiate with nectar spur. Flowering is acropetally toward apex. Flowers are persistent and not fragrant.

*Flower size.*—Length: Approximately 1.9 cm. Width: Approximately 1.6 cm. Depth, including nectar spur: Approximately 1.2 cm.

*Aspect.*—Facing outward and upward.

*Petals.*—Quantity: Five per flower. The upper four petals are fused at base forming a lip having two central linear lobes and one outer obovate lobe on each side. The lower petal has two obovate lobes and is modified into a nectar spur. All lobes have rounded tips and entire margins. Spur length: 7 mm. Spur diameter at base: 2 mm. Spur diameter at tip: 1 mm. Spur texture: Glabrous. Spur color: 160B at base, 160D at tip.

*Petal color.*—When first open, the upper surface of all lobes is closest to N87A with palate of 8A. Lower surface is closest to N88C. Upper surface of mature lobes is between N87B and N87C with palate of 8A. Lower surface is closest to N88D.

*Peduncle.*—Shape: Square in cross section. Strength: Strong, wiry. Angle to the stem: Acute. Length: Approximately 2.2 cm. Diameter: Approximately 1 mm. Texture: Densely pubescent. Color: 144A.

*Pedicel.*—Strength: Good. Angle to stem: Acute. Length: Approximately 1.1 cm. Diameter: Approximately 0.8 mm. Texture: Dense short, soft, glandular pubescence. Color: Slightly lighter than 144A.

*Bud.*—Shape: Ovoid with spur. Length: Approximately 1 mm. Diameter: Approximately 6 mm. Texture: Glabrous. Color: Closest to 83C.

*Calyx.*—Shape: Star shaped, formed by five sepals fused at base. Width at base: Approximately 1 mm. Width at apex: Approximately 4 mm. Sepal shape: Lanceolate. Sepal margin: Entire. Sepal apex: Acute. Sepal length: Approximately 3.5 mm. Sepal width: Approximately 1 mm. Sepal texture: Upper surface is glabrous. Lower surface is densely pubescent. Sepal color: Both surfaces: 144B.

*Reproductive organs.*—Androecium: There are 4 stamens per flower, 2 are 3 mm in length and 2 are 2 mm in length. Filament shape: Curved around pistil. Anther shape: Oval. Anther length: 1 mm. Anther color: 11C. Amount of pollen: Abundant. Pollen color: 11B. Gynoecium: Number: One pistil per flower. Pistil length: 2 mm. Stigma length: Less than 1 mm. Stigma color: 150C. Style length: Less than 1 mm. Style color: 150D. Ovary diameter: 1 mm. Ovary color: N144C.

Seed and fruit production: Neither seed nor fruit production has been observed.

Disease and pest resistance: Resistance to pathogens and pests common to *Nemesia* has not been observed.

What is claimed is:

1. A new and distinct cultivar of *Nemesia* plant named 'Balarimdep', substantially as herein shown and described.

* * * * *